(12) United States Patent
Ward et al.

(10) Patent No.: US 9,271,738 B2
(45) Date of Patent: Mar. 1, 2016

(54) DEVICE FOR CONTROL OF DIFFICULT TO COMPRESS HEMORRHAGE

(75) Inventors: Kevin R. Ward, Richmond, VA (US); Mark Licata, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 491 days.

(21) Appl. No.: 12/601,706

(22) PCT Filed: May 30, 2008

(86) PCT No.: PCT/US2008/065238
§ 371 (c)(1),
(2), (4) Date: Nov. 24, 2009

(87) PCT Pub. No.: WO2008/150966
PCT Pub. Date: Dec. 11, 2008

(65) Prior Publication Data
US 2010/0179586 A1    Jul. 15, 2010

Related U.S. Application Data

(60) Provisional application No. 60/941,313, filed on Jun. 1, 2007.

(51) Int. Cl.
*A61B 17/00* (2006.01)
*A61B 17/132* (2006.01)
(Continued)

(52) U.S. Cl.
CPC ............. *A61B 17/1325* (2013.01); *A61B 17/12* (2013.01); *A61B 17/135* (2013.01); *A61B 17/1322* (2013.01)

(58) Field of Classification Search
CPC .. A61B 17/12; A61B 17/1325; A61B 17/135; A61B 17/132; A61B 17/1322; A61B 17/1355; A61B 5/02233; A61B 17/1327; A61H 9/0078; A61H 2201/5074
USPC .......... 606/201–203; 600/490, 499; 128/96.1, 128/869–870; 60/201–203
See application file for complete search history.

(56) References Cited

U.S. PATENT DOCUMENTS 3,454,010 A * 7/1969 Miller et al. .................. 606/202
3,933,150 A    1/1976 Kaplan
(Continued)

FOREIGN PATENT DOCUMENTS

DE           20300739      * 5/2003

OTHER PUBLICATIONS

Soltan, M. H., et al., "External aortic compression device: The first aid for postpartum hemorrhage control." J. Obstet. Gynaecol. Res. vol. 35, No. 3: 453-458. Jun. 2009.
(Continued)

*Primary Examiner* — Amy R Weisberg
(74) *Attorney, Agent, or Firm* — Marshall, Gerstein & Borun LLP

(57) ABSTRACT

Bleeding from blood vessels located in difficult-to-compress regions of the body (especially the abdomen, pelvic or groin region) is controlled by the use of a portable, small-footprint belt-like device that contains multiple inflatable bladders. The inflatable bladders are selectively positioned and inflated over exsanguinating blood vessels, thereby exerting pressure to stop the bleeding. The device may also be used to provide perfusion support in low flow disease states such as hemorrhagic shock and cardiac arrest.

11 Claims, 12 Drawing Sheets

(51) Int. Cl.
*A61B 17/135* (2006.01)
*A61B 17/12* (2006.01)

(56) References Cited

U.S. PATENT DOCUMENTS

| | | | | |
|---|---|---|---|---|
| 4,233,980 | A * | 11/1980 | McRae et al. | 606/201 |
| 4,321,929 | A * | 3/1982 | Lemelson et al. | 600/301 |
| 4,577,622 | A * | 3/1986 | Jennings | 601/134 |
| 4,580,555 | A * | 4/1986 | Coppess | 602/23 |
| 4,671,290 | A * | 6/1987 | Miller et al. | 600/494 |
| 4,773,419 | A * | 9/1988 | Tountas | 606/202 |
| 4,928,674 | A * | 5/1990 | Halperin et al. | 601/44 |
| 5,062,414 | A * | 11/1991 | Grim | 602/19 |
| 5,122,111 | A * | 6/1992 | Sebastian et al. | 602/19 |
| 5,338,239 | A * | 8/1994 | Cleaveland | 441/106 |
| 5,383,893 | A * | 1/1995 | Daneshvar | 606/201 |
| 5,383,920 | A * | 1/1995 | Sikes | 607/112 |
| 5,645,563 | A * | 7/1997 | Hahn et al. | 606/202 |
| 5,665,057 | A * | 9/1997 | Murphy | 602/19 |
| 5,704,904 | A * | 1/1998 | Dunfee | 602/13 |
| 5,707,177 | A * | 1/1998 | Lehrer et al. | 405/186 |
| 5,741,295 | A | 4/1998 | McEwen | |
| 5,743,864 | A | 4/1998 | Baldwin | |
| 5,799,650 | A * | 9/1998 | Harris | 128/96.1 |
| 5,830,168 | A * | 11/1998 | Finnell et al. | 602/24 |
| 5,893,368 | A * | 4/1999 | Sugerman | 128/898 |
| 6,007,559 | A * | 12/1999 | Arkans | 606/201 |
| 6,065,166 | A * | 5/2000 | Sharrock et al. | 5/630 |
| 6,066,109 | A * | 5/2000 | Buser et al. | 602/23 |
| 6,179,796 | B1 * | 1/2001 | Waldridge | 601/149 |
| 6,189,538 | B1 * | 2/2001 | Thorpe | 128/898 |
| 6,264,673 | B1 | 7/2001 | Egnelov | |
| 6,503,217 | B1 * | 1/2003 | Gibbs et al. | 602/23 |
| 6,616,620 | B2 * | 9/2003 | Sherman et al. | 601/41 |
| 6,626,856 | B2 * | 9/2003 | Manoach | 602/5 |
| 6,939,314 | B2 * | 9/2005 | Hall et al. | 601/41 |
| 7,329,792 | B2 | 2/2008 | Buckman | |
| 7,574,761 | B2 * | 8/2009 | Davis | 5/710 |
| 7,677,605 | B2 * | 3/2010 | Cook et al. | 285/256 |
| 7,931,607 | B2 * | 4/2011 | Biondo et al. | 602/13 |
| 8,142,378 | B2 * | 3/2012 | Reis et al. | 602/13 |
| 2002/0144343 | A1 * | 10/2002 | Kuiper et al. | 5/81.1 R |
| 2003/0176825 | A1 * | 9/2003 | Yavnai | 602/13 |
| 2004/0147956 | A1 * | 7/2004 | Hovanes et al. | 606/202 |
| 2007/0117479 | A1 * | 5/2007 | Weinel et al. | 441/117 |
| 2007/0282230 | A1 * | 12/2007 | Valderrabano et al. | 601/152 |
| 2008/0004555 | A1 * | 1/2008 | Reis et al. | 602/13 |
| 2008/0281351 | A1 * | 11/2008 | Croushorn et al. | 606/202 |
| 2012/0150215 | A1 | 6/2012 | Donald | |
| 2013/0041303 | A1 | 2/2013 | Hopman et al. | |
| 2013/0296921 | A1 | 11/2013 | Saunders et al. | |

OTHER PUBLICATIONS

Miller, S., et al., "Anti-shock garment in postpartum haemorrhage." Best Practice & Research Clinical Obstetrics and Gynaecology. vol. 22, No. 6. pp. 1057-1074, 2008.

C. Brees, et al., "A non-inflatable anti-shock garment for obstetric hemorrhage." International Journal of Gynecology and Obstetrics. 2004 87, 119-124.

Miller, S., et al., "A comparative study of the non-pneumatic anti-shock garment for the treatment of obstetric hemorrhage in Egypt." International Journal of Gynecology and Obstetrics. 109 (2010) 20-24.

Kragh, John F., et al., "New Tourniquet Device Concepts for Battlefield Hemorrhage Control." The Army Medical Department Journal. Apr.-Jun. 2011, pp. 38-46.

Miller, S., et al., "A comparative study of the non-pneumatic anti-shock garment for the treatment of obstetric hemorrhage in Nigeria." International Journal of Gynecology and Obstetrics. 107 (2009) 121-125.

Taylor, et al. "The Evaluation of an Abdominal Aortic Tourniquet for the Control of Pelvic and Lower Limb Hemorrhage," Military Medicine 178(11):1196-1201 (2013).

* cited by examiner

DEVICE FOR CONTROL OF DIFFICULT TO COMPRESS HEMORRHAGE

CROSS-REFERENCE TO RELATED APPLICATIONS

This application is a United States national stage application under 35 U.S.C. §371 of PCT Application No. PCT/US08/65238 designating the United States, filed on filed May 30, 2008, which claims benefit of U.S. Provisional Application No. 60/941,313, filed Jun. 1, 2007, each of which is hereby incorporated by reference.

BACKGROUND OF THE INVENTION

1. Field of the Invention

The invention generally relates to controlling bleeding from severed or damaged peripheral blood vessels that are located in an area where it is difficult to apply conventional compression, such as the abdomen, pelvic or groin region. In particular, the invention provides a portable, small-footprint device with inflatable bladders that can be selectively positioned and inflated to exert pressure over peripheral blood vessels to stop exsanguination. In addition, the device may be used to assist in increasing perfusion pressure to the heart and brain in a number of disease sates such as hemorrhagic shock, cardiogenic shock, and cardiac arrest.

2. Background of the Invention

Hemorrhage from vascular injuries in the proximal extremities, pelvis, and abdomen is extremely difficult to treat. While the treatment of such injuries is challenging when they occur in civilian populations, they are even more difficult to treat in combat situations. While improvements in body armor have reduced mortality from combat injuries to the chest, the incidence of penetrating injuries to the extremity and their associated mortality remain high. It has been estimated that a well-designed battlefield tourniquet could potentially prevent 10% of all combat deaths due to exsanguinating peripheral vascular wounds. While it is gratifying that recent robust efforts have developed to create better tourniquets for treatment of these wounds, there remains a very important subset of lower extremity wounds in the region of the groin that cannot be treated with traditional tourniquets. Although the exact percentage of these wounds are unknown, both military and civilian reports detail the challenges in controlling ongoing hemorrhage of vascular injuries in this anatomical area especially in the pre-surgical time period.

Clearly, wounds to the groin, pelvis, and abdomen are complex and may involve several systems either alone or in combination, including major vascular structures, the bony pelvis, solid organs such as the liver and spleen, and even hollow organ injury to the bowel and bladder. Wounds directly involving isolated major vascular structures above the level of the femoral artery and vein such as the iliac artery and veins are most challenging to deal with followed by complex bony pelvic injuries from high velocity penetrating trauma resulting in complex arterial and lower pressure venous bleeding similar to those of blunt pelvic injuries experienced in a civilian trauma center.

Lastly even injuries involving isolated major vascular injury at or just above the inguinal ligament pose a tremendous field challenge in creating hemostasis. The femoral artery is usually palpable at the level of the inguinal ligament. Despite this, the ability to control bleeding by application of direct pressure by either the injured combatant or by others including fellow soldiers or medic aides will usually not suffice especially if rapid manual transport must take place. Controlling hemorrhage by application of direct manual pressure may be particularly challenging in cases where there is no large tissue defect allowing for packing and more pressure in closer proximity to the injured vessels. In fact, currently the only way to address this is by exploring the wound site, locating the artery and clamping it with hemostats. For deeper vascular injuries to the pelvis and abdomen, exploration is not an option until the time of surgery.

Similarly, cardiopulmonary resuscitation (CPR) to "restart" the heart of an injured patient is frequently necessary in emergency situations. During the period of time when a heart is not beating, and until it regains the ability to do so, it is imperative that respiration (i.e. lung inflation and deflation) be maintained so that blood circulation continues. It is especially essential to maintain blood circulation to the heart and brain during this time, or serious irreversible damage can occur. Even when a trained first aid provider performs chest compressions is these circumstances, blood flow in the victim is still well below normal (e.g. 20-30%). Thus, there is an ongoing need to provide adjunct therapies and devices that can aid in maintaining adequate blood flow during emergency situations that require CPR. In particular, it would be of benefit to have available a low-cost, portable, small footprint device that could be rapidly utilized in a straight forward manner. It would be especially desirable to have available a device with these attributes that could be used for both 1) the control of bleeding and 2) as an aid to CPR.

U.S. Pat. No. 3,933,150 to Kaplan et al. teaches an apparatus for the treatment of shock. The apparatus includes a single piece of double-walled material that can receive pressurized gas. Inflation of the device causes pressure to be exerted on an individual wearing the apparatus, thereby decreasing the volume of pooled venous blood and stabilizing the individual during transport. However, the pressure is exerted is globally or circumferentially and is not specifically directed onto the bleeding site, and thus does little for bleeding from locations that are difficult to access.

U.S. Pat. No. 7,329,792 to Buckman et al., discloses an apparatus for promoting hemostasis, especially of skin-penetrating wounds of the periphery. The device includes fluid impermeable barriers surrounded by exterior dams to be held in place over a wound by applied force. However, such devices are not suited to promote hemostasis in regions that are difficult and thus where it is difficult to exert pressure.

U.S. Pat. No. 6,939,314 to Hall et al. teaches an automatic chest compression system, for example, during CPR. The system utilizes a bladder that is comprised of a plurality of individual sections that are preferentially in fluid communication with each other. When the bladder is disposed over the sternum of a patient and inflated (e.g. with a gas or fluid), pressure is exerted on the chest of the patient. However, the positions of the sections of the bladder are fixed with respect to each other and thus the device does not provide flexibility with respect to positioning of the bladder sections. This device would not be suitable for use, for example, to control bleeding in regions where it is difficult to exert pressure, such as the groin.

U.S. Pat. No. 5,743,864 to Baldwin discloses an apparatus for performing cardio-pulmonary resuscitation with active reshaping of a patient's chest. However, the apparatus requires a piston as the driving force for compression, and is clearly not designed for easy storage and transport for use in the field, and the technology is not transferable to use in controlling bleeding in regions where it is difficult to exert pressure.

The prior art has thus far failed to provide a device to aid in the temporary isolation and occlusion of an artery by the application of precisely directed pressure. In particular, the prior art has not provided a device that can be so-used that can also be employed as an adjunct to provide chest compression during CPR.

SUMMARY OF THE INVENTION

The present invention provides a portable, compact device that can be used to selectively exert pressure on areas of the body of an injured individual where it is otherwise difficult to do so. In particular, the device may be used to stop bleeding from difficult areas such as the groin, pelvis and abdomen. The device is low-cost and portable, has a small footprint, and can be readily and rapidly deployed by a lay individual (or even by an injured person) making it especially useful, for example, in combat or other situations where emergency treatment needs to be administered "on the fly". Significantly, the device is multi-functional and can also be advantageously employed to generate pressure on other areas of the body, for example, on the chest and/or abdominal cavity during CPR.

The device comprises a plurality of individual, inflatable, movable bladders attached to a supporting flexible belt-, strap-, or wrap-like portion (member) of the device. The bladders are movably attached to the support portion in a manner that allows each bladder to be individually positioned along or within the device, and thus over a desired area or region of a body to which the device has been attached. Once positioned, a bladder is then inflated to exert continuous, intense and evenly distributed pressure on the area under the bladder. By positioning and inflating a plurality of bladders, pressure can be applied to more than one area, or to adjacent areas, in a highly specific or directed manner. The ability to apply significant pressure to specific, selected locations, rather than globally or simply circumferentially as is taught in prior art devices, allows the application of narrowly focused pressure where it is most needed. For example, blood vessels located beneath the area that is covered by an inflated bladder are compressed and hemorrhage from those vessels is decreased or prevented. Thus, using the device of the invention, damaged blood vessels located in even hard to reach areas such as the groin can be selectively targeted for compression.

Advantages of the device include:
1) The device is highly portable, having a very small footprint that allows it to be folded and carried by an individual, e.g. a soldier, or for several to be carried by a medic or other health professional;
2) All components of the device are "ruggedized", i.e. constructed of heavy duty materials that are not easily punctured or otherwise damaged;
3) The relative simplicity of the device allows rapid application even by those who do not necessarily have professional medical training, potentially even by a wounded individual him- or herself;
4) Application of the device allows for rapid transport of a wounded individual without destabilizing the device;
5) The extent of inflation of the bladders, both with regard to which and how many bladders are inflated, and how much they are inflated, allows for titration of the response to the injury;
6) In most cases, the devices are re-usable;
7) The devices are very low in cost;
8) In addition to stopping or decreasing bleeding, the devices also stabilize the area where they are applied (e.g. pelvic region), thereby preventing further damage.

The invention thus provides a medical compress device, comprising: a support member securable to a patient, the support member having at least two ends separated by a length dimension; one or more inflatable bladders attached to the support member, the inflatable bladders being selectively inflatable and deflatable, and positionable at multiple locations along the length of the support member; and further, when at least two ends of the support member are joined together to attach the support member to the patient and the one or more inflatable bladders are positioned at one or more selected locations of the multiple locations along the length of the support member and are inflated, a compressive force is exerted on the patient in at least one specific area on the patient. In some embodiments, the support member is comprised of one or more belts or straps. Further, the support member may include a channel formed in the one or more belts which extends along at least a portion of the length of the support member, and wherein the one or more inflatable bladders may include an attachment knob which includes a portion which fits within the channel. The channels in effect may form a grid allowing for movement of the bladders in the X and Y planes at will, e.g. along both the length and width of a strap. In some embodiments of the invention, the one or more bladders have length and width dimensions which are the same as or different from each other, and the one or more bladders are rotatable about the attachment knob (e.g. up to 360°) relative to the one or more belts.

In further embodiments, the support member includes a channel forming member attached to the one or more belts which extends along at least a portion of the length of the support member. In this case, the one or more inflatable bladders includes an attachment knob which includes a portion which fits within the channel forming member. In this embodiment, the one or more bladders may have length and width dimensions which are different from each other, and the one or more bladders may be rotatable about the attachment knob (e.g. up to 360°) relative to the one or more belts.

In other embodiments of the invention, the support member of the medical compress device is comprised of at least two belts and at least one of the one or more inflatable bladders is secured to both of the two belts. In yet other embodiments, the support member is comprised of at least two belts, and further comprises one or more connecting members which connect the at least two belts together at specified locations along the length of each of the at least two belts. In addition, one or more barriers may be positioned at specified locations along the length of the support member, in order to restrict movement of the one or more inflatable bladders to defined portions along the length of the support member. In further embodiments of the invention, the one or more inflatable members are slidable along the length of the support member, and/or "up and down" along the width of the support member.

In some embodiments, the medical compress device of the invention comprises a pump connectable to at least one of the one or more inflatable bladders for inflating the one or more inflatable bladders. The pump may include a valve for deflating at least one of the one or more inflatable bladders. In addition, the device may include a pressure sensor connectable to at least one of the one or more inflatable bladders.

In yet other embodiments, the medical compress device includes at least one connecting member positioned at one end of the at least two ends of the support member. Further, at least one connecting member may include two connecting members which selectively join together and detach from each other, wherein one of the two connecting members is joined to each of the two ends of the support member. The medical compress device of the invention may further comprise at least one tightening member associated with at least a portion of the support member for tightening the support member on the patient after the two ends of the support member are joined together.

In other embodiments of the invention, the support member of the medical compress device is comprised of at least two belts and may further comprise one or more sliding straps, wherein the one or more sliding straps are slidably connected to each of the at least two belts and are slidable along the at least two belts, and wherein at least one of the one or more inflatable bladders is secured to the one or more sliding straps. In some embodiments, at least one of the one or more inflatable members is secured to at least one of the two sliding straps.

DETAILED DESCRIPTION OF THE PREFERRED

Embodiments of the Invention

Figure 1A:
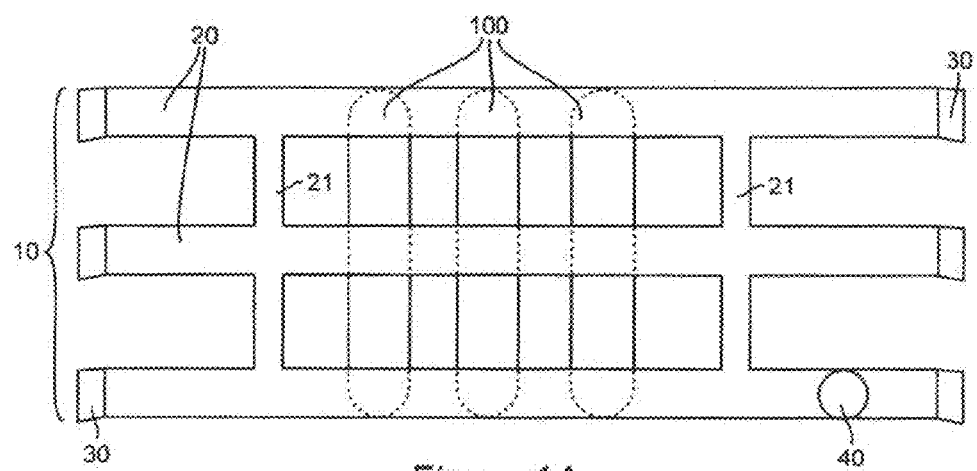
FIG. 1A-E. Exemplary schematic representations of the device or apparatus of the invention. A, device comprising belts or straps; B, device comprising a band of flexible material; C, device with bladders disposed in pockets; D, alternative device with bladders disposed in pockets; E, exemplary inflatable bladder.

The present invention provides a portable, small-footprint device that can be used to selectively exert pressure on the body of an injured individual. The device is especially useful in emergency situations, and particularly to apply pressure to areas of the body where it is otherwise difficult to do so. The device or garment is generally in the form of a flexible support portion (comprising e.g. one or more belts, straps, bands, wraps, etc., all of which are referred to interchangeably and are collectively referred to as "belts" or "straps") that can be circumferentially attached or secured to an area of the body of an individual in need of applied pressure (e.g. the pelvic area, abdominal area, the chest area, etc.). A plurality of inflatable bladders are associated with the support portion of the device, i.e. the bladders are attached to the support portion of the device. The attached bladders are however, not stationary. Instead, they are movable or positionable on the support portion i.e. the locations of the bladders on the device are not fixed but are mobile or adjustable. After the device is placed on an individual, each individual bladder can be independently positioned by adjusting its location on the device, and each can be independently inflated. As a result, each bladder can be moved to encompass or cover a defined location on the body of an individual to whom the device is attached. Upon inflation of a bladder, intense pressure is evenly distributed to the area immediately beneath the inflated bladder. Counter-expansion away from the body's surface is prevented or significantly decreased by the nonexpandable nature of the straps to which the bladders are attached, i.e. the straps retain their dimensions and do not "stretch". This is distinctly different from such devices as the pneumatic antishock garments which provide for only circumferential pressure, or newer pelvic stabilizing devices such as the Traumatic Pelvic Orthotic Device (BioCybernetics International) or the SAM Pelvic Sling (SAM Medical Products). These latter two devices provide for pelvic stabilization but not downward pressure into the groin or pelvic cavity for hemostasis.

The pressure exerted by the inflated bladders may be intensified by additional tightening of components (e.g. straps or belts) of the support portion of the device using a tightening means. The benefits of the pressure will vary from application to application. For example, in the case of uncontrolled bleeding from a non-compressible or difficult to compress location, blood vessels in the area are compressed, and bleeding from the compressed vessels is decreased or stopped. In one embodiment, the device is designed to be applied to peripheral areas such as the pelvic region (e.g. inguinal or groin area) to stop bleeding from, for example, femoral and external iliac blood vessels.

Another salubrious effect of the inflated device is that it also provides support (i.e. stability or rigidity) to the region of the body that it encircles. In fact, the device may be employed chiefly to provide stability and/or pressure, whether or not bleeding is present. For example, in one embodiment described in detail below, the device is used as an adjunct to CPR. In this embodiment, application of the device to the chest prevents chest expansion e.g. in response to mechanical ventilation thereby increasing intrathoracic pressure; and/or application of the device to the abdomen restricts blood flow into the abdomen from the chest. Blood is thus directed to where it is most needed, i.e. to the heart or brain of the patient.

The deployment of the device is rapid and can be carried out by individuals with very little prior training. In fact, a wounded individual in need of such treatment may be able to deploy the device him or herself. The device may thus be used to provide support and/or to stop or lessen bleeding at a trauma site (e.g. on the battlefield, or at the scene of an accident) and during transport to a clinic or hospital where further medical treatment can be provided.

FIGS. 1A-D show schematic, generalized representations of the device of the invention. FIG. 1A illustrates an embodiment in which flexible portion or support 10 comprises multiple (in this case 3) straps 20, which are strap- or belt-like in form. The number of straps in an embodiment of this type may be vary, but will generally range from about 1 to about 10, and preferably from about 2 to about 5, and most preferably will be about 3 or 4. Straps or belts 20 are typically made from ruggidized fabric, i.e. tough and durable yet flexible materials such as various types of commercial grade webbing or strapping (e.g. nylon, cotton, polypropylene, polyester, polypropylene/polyester, etc.), canvas, and the like. In one embodiment, flexible nylon webbing such as that used in the manufacture of seat belts is employed. While the material is flexible, it does not stretch, elongate, or deform in response to stress, but essentially retains its original dimensions. In other words, the webbing or strapping material is bendable and can be wrapped around an object, thereby substantially conforming to the shape of the object (e.g. a human body or portion thereof), but the dimensions of the webbing are substantially fixed and the webbing is strong enough to withstand force up to at least about 500 mm Hg. The straps are thus capable of being tightened securely on the body of an individual, and to help in developing and maintaining the pressure that is exerted via an inflated bladder. Generally, the dimensions of strap 20 will be in the order of about ½ to about 62 inches in width, and preferably about 2 to about 4 inches in width; and the length of strap 20 will range from about 10 to about 80 inches, and preferably from about 40 to about 60 inches in length. The thickness will generally be in the range of from about 0.1 to about 10 mm. Straps 20 may be interconnected (connected to each other) by connecting elements 21 to form a web or other configuration. Connecting elements 21 are generally disposed between straps 20 in a manner that holds the plurality of straps apart from each other and yet in proximity to each other, e.g. with a space of from about 1-5 inches, preferably about 2-3 inches, between adjacent straps 20. In some embodiments, connecting elements 21 are fashioned from the same or similar material as straps 20, and may contain channels for accommodating and adjusting the position of inflatable bladders. However, those of skill in the art will recognize that in other embodiments, connecting elements 21 may differ from straps 20 and may be, for example, in the form of loops, rings or chains made from ruggidized fabric, plastic, metal, etc. Alternatively, connecting elements 21 may be of a cylindrical ropelike design so as to resemble, e.g. twine or a slender rope. Further, connecting elements may or may not be flexible, i.e. they may be stiffer than straps 20. Connecting elements 21 are intended to hold straps 20 together so the general shape of the device is that of a net or web of straps. Generally, the straps 20 must be flexible in order to conform to the contours of the body on which the device is placed, i.e. straps 20 wrap around the body or around a particular part of the body (e.g. pelvis, chest, leg, arm, etc.) whereas connecting elements 21 cover a much smaller area and do not necessarily need to flex. Thus, flexibility of connecting elements 21 is optional.

In addition, additional straps or belts 20 may be added to further secure the device, e.g. straps that go over the shoulder, that pass from back to front through the groin area, etc.

One or more inflatable bladders 100 are moveably or positionably attached to device 10. Generally the number of bladders per device will be from about 1 to about 10 or more. While any number of bladders may be used, the number will preferably range from about 2 to about 5, and most preferably will be from about 3 or 4 per device. If three or more bladders are utilized, this allows placement of one bladder over each side of the groin and one over the suprapubic area or in another orientation as desired by the user. In this case, such a device would allow control of femoral artery bleeding even in the transected and retracted artery since the bladders would span the length of the artery at that level. The device may also allow for control of deeper pelvic artery and venous bleeding through either direct pressure by the bladder or by stabilizing the bony pelvis.

In general, the dimensions of inflatable bladder 100 are in the range of from about 1-15 inches in width and from about 2-12 inches in length, and preferably about 2-8 inches in width and/or length, and are substantially rectangular in shape. However, bladders of other shapes (e.g. square, circular, irregular multilateral, etc.) may also be employed. The dimensions (e.g. the length, width, thickness, etc.) of a bladder may be the same or different. Inflatable bladders 100 are constructed of at least two layers of material with a cavity disposed there between. The material used to construct the bladders is extremely durable, puncture-proof material that is at least somewhat flexible or malleable, and can expand upon introduction of pressurized gas (e.g. air) into the cavity. Examples of such materials include but are not limited to various plastics and rubbers, and other suitable materials that are known to those of skill in the art. The cavity is designed to receive (i.e. be inflated by) a pressurized gas and to maintain a desired pressure within the inflatable bladder 100 indefinitely, or until deflation of the bladder and release of the gas is desired. Generally, the bladder is able to maintain a pressure of at least about 10-180 mmHg, and preferably at least about 180-200 mmHg, and even more preferably at least about 200-500 mmHg throughout the period of inflation. In the practice of the present invention, inflatable bladders 100 may be specifically designed and manufactured for use in the device. Alternatively, several "off the shelf" items exist that can be used directly or further adapted for use in the device. For example, bags that are used for the administration of intravenous (IV) fluids (i.e. those which are typically suspended and used to gravity feed IV fluids to a patient) may be used as inflatable bladders. If multiple inflatable bladders are attached to the device, they may be of the same or similar size (dimensions) and shape, or the inflatable bladders may differ from one another in size and shape.

Figure 1B:
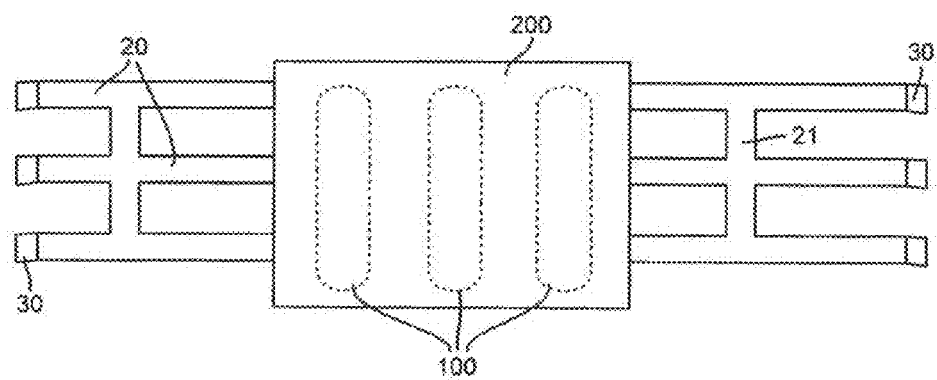
Figure 1C:
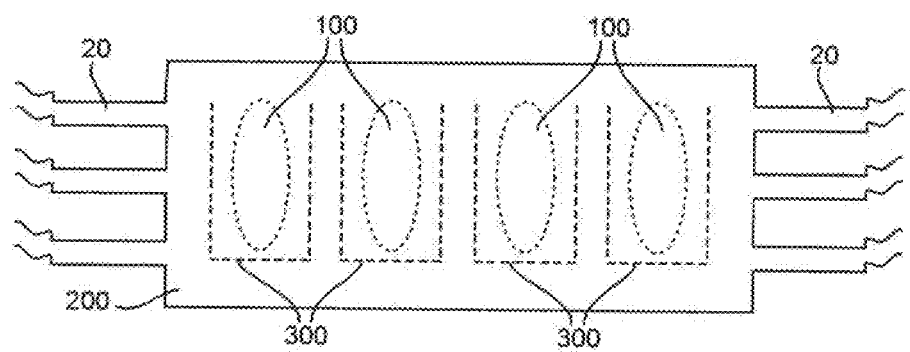
Figure 1D:
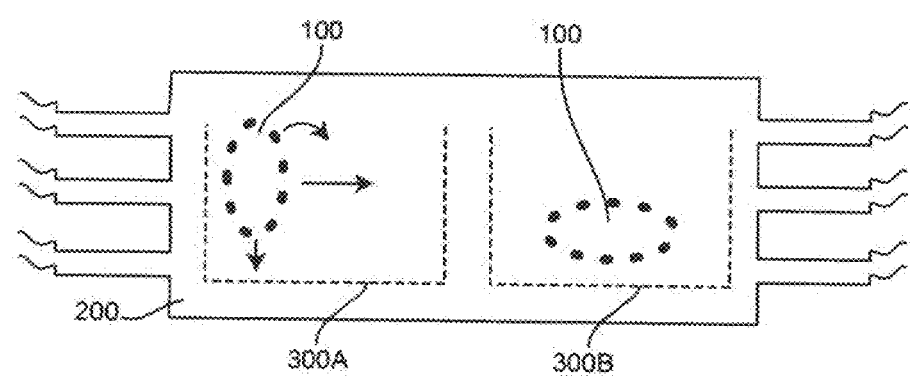
Figure 1E:
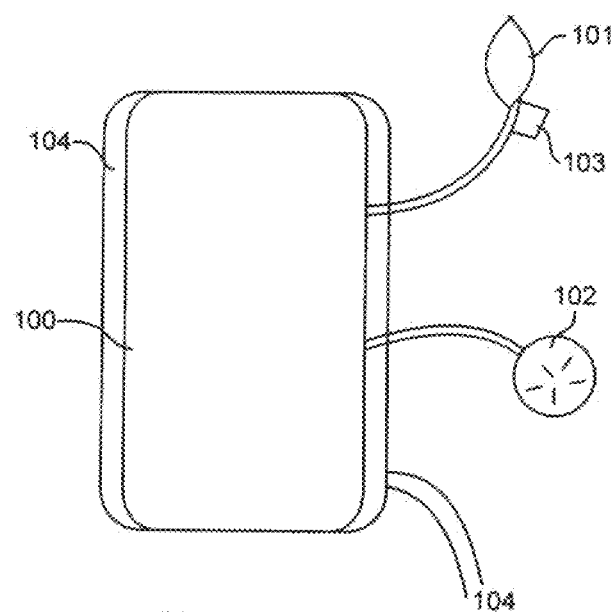

With reference to FIG. 1E, inflatable bladder 100 is typically fitted with a means for providing pressurized gas 101 (e.g. a hand pump) and a means of monitoring the pressure 102 (i.e. a pressure sensor) during and after inflation. In one embodiment of the invention, the means for providing pressurized gas can be a hand-operated bulb such as is used with traditional manually-inflated sphygmomanometers (blood pressure cuffs). Alternatively, foot operated pumps such as those used to inflate larger bladder devices such as swimming pool flotation devices may be used. Other means of providing pressurized gas include but are not limited to various pumps such as those that are used for manual inflation of bicycle tires and basketballs, syringe-like devices with a plunger mechanism to compress and drive gas into a receptacle, etc. Preferably, the means of pressurizing gas is small enough to be readily incorporated into the small footprint of the portable device. While the device of the invention is generally used in situations where the only source of gas to pressurize is ambient air, this need not always be the case. The device may also be employed in situations where pressurized gas (e.g. compressed air or other inert gas) is available and such sources may also be used to inflate the bladders. Further, if automated sources of pressurized gas are available, these may be employed.

In addition, in some embodiments, the device comprises a feedback means 104. Such a feedback means or mechanism may be, for example, a closed feedback loop whereby the application of pressure is linked (e.g. electronically) to a value of for example, a patient's vital signs such as blood pressure, heart rate, pulse, etc. Thus, the extent of inflation of one or more bladders and one or more of a patient's vital signs are monitored (e.g. electronically) and the extent of inflation of one or more bladders, and hence the amount of pressure that is exerted, is adjusted automatically based on predetermined instructions. For example, if the patient's blood pressure falls below a predetermined value, the means for inflation will automatically increase the inflation of one or more bladders until a more favorable predetermined blood pressure value is detected.

Those of skill in the art will recognize that many types of means for monitoring pressure are available and are designed on a scale that would be appropriate for incorporation into the small footprint device of the portable device. In one embodiment, the means is a dial-type pressure gauge such as those which are used with hand-operated blood pressure cuffs. Alternatively, a digital monitor may be used. Other examples include but are not limited to color coded springs that are calibrated and protrude from or extend out of the pressure device in response to various pressures, etc.

Those of skill in the art will recognize that many alternatives exist for attaching pressurizing means 101 and measuring means 102 to inflatable bladder 100. For example, various screw or snap mechanisms exist which are air tight are known to those of skill in the art. Further, some means of switching from a state of inflation to a state of deflation and vice versa is also generally included in the device. For example, if a traditional bulb-style hand pump (as is used with blood pressure cuffs) is utilized, such a bulb is typically equipped with a valve 103 that is closed during inflation and opened during deflation. Other mechanisms for controlling the flow of pressurized air into and out of the bladder include but are not limited to computerized pumps with pressure sensing solenoid valves that allow for pressure compensation in response to movement or leakage, etc.

While the support portion of the device of the invention may be constructed principally of strap or belt-like elements, as depicted in FIG. 1A, other designs may also be used. For example, FIG. 1B depicts a device constructed of straps 20 and connecting elements 21 but which includes and a wider band 200 of ruggidized, flexible material. In this embodiment, inflatable bladders 100 (shown in phantom) are attached to band 200 rather than to straps 20. Straps 20 may either attach to the edges of band 200, or band 200 may be superimposed over and cover straps 20, i.e. band 200 may be affixed to straps 20. In yet other embodiments, the device may be fashioned of a single band of material to which the inflatable bladders are attached. In addition, the support portion may be comprised in part or completely of one or more rope- or twine-like straps or bands; various chains (e.g. interlocking rings of plastic, metal, fabric, etc.); strips or bands of real or synthetic leather; straps, bands or fabric made of wool, silk, bamboo, sheepskin, etc.

Yet another embodiment of the device is depicted in FIGS. 1C and D. In this embodiment, the device of the invention comprises one or more pockets or pouches 300 (shown in phantom by dashed lines), and inflatable bladders 100 (shown in phantom by dotted lines) are disposed within the pockets 300. A single pocket may contain one or more than one inflatable bladder. With reference to FIG. 1C, each pocket 300 contains an inflatable bladder 100. After the device is placed on an individual, the available bladders are selectively inflated, i.e. one or more or all of the bladders are inflated, according to the needs of the patient. For example, in the device depicted in FIG. 1C, if band 200 spans the entire pelvic region of the patient, 1, 2, 3 or all 4 of the bladders may be inflated, depending on whether bleeding is occurring from the right or left arteries, or both, and whether pressure is desired on the right, or left, or over all the pelvic area. While FIG. 1C depicts a single row of pockets 300, multiple rows may be included. Further the rows may extend completely around the device. In addition, pockets 300 may be attached to a wide band of material as shown in FIG. 1C, or to a single narrower strap 20, or to multiple straps, e.g. sewn or otherwise attached across two or more straps of the device. One advantage of this embodiment is that the device may be reused many times and any damaged or missing bladders may be replaced as needed. Alternatively, one or more bladders 100 may be placed in pockets 300 of the device just before or even after the device is fitted onto an individual. Deflated bladders may be stored off the device in a separate container, or in another compartment on the device, etc. Deflated bladders are then selected at the time of use, and placed in one or more selected pockets 300 where they are likely to do the most good when inflated.

In one variation of this embodiment, depicted in FIG. 1D, at least one bladder 100 is disposed within a pocket 300, the dimensions of which exceed those of bladder 100. In this embodiment, the position of bladder 100 within pocket 300 can be adjusted, e.g. by sliding horizontally from left to right within the pocket, by sliding vertically up and down within the pocket, or by rotating within the pocket. These possibilities are illustrated by the arrows in packet 300A, which shows an inflatable bladder 100 with its long axis in a vertical position. On the other hand, pocket 300B contains bladder 100 with its long axis in a horizontal position. Those of skill in the art will recognize that, depending on the dimensions of pocket 300 and bladder 100, the position of bladder 100 may be conveniently adjusted anywhere within pocket 300.

To that end, pocket 300 may be formed from material that has some potential to stretch or "give" so that bladders are held in place prior to inflation, but may still be inflated to capacity while in the pocket. Alternatively, pocket 300 may be large enough to accommodate an inflated bladder but at least one side of pocket 300 may be reversibly closeable by, e.g. a velcro closure, a button, an elasticized seam, a gathered seam (i.e. a seam that is gathered by pulling a string), or some other means that affords ready opening and closing of the pocket, in order to place and retain deflated bladders within the pocket, and yet allow inflation sufficient to exert efficacious pressure where needed.

Those of skill in the art will recognize that many such configurations of the device exist, and that many materials may be used to fashion the device. All such configurations and designs are intended to be encompassed by the present invention.

As illustrated in FIGS. 1A and B, one or more securing means 30 are provided on the device to secure opposing ends of support portion 10 to each other, thereby securing the device to an individual. In the case in which flexible support portion 10 comprises multiple straps, each strap typically comprises a securing means 30, although this need not be the case. For example, one portion of the securing means may attach to multiple straps, and be able to receive multiple interlocking mating portions from a plurality of straps on the opposing end of the device. Various suitable fastening, locking, buckling, or snapping mechanisms exist which may be suitable for use in the present invention, and any suitable mechanical connection may be used in the practice of the invention. Securing means 30 will generally comprise two connectable parts which, when connected to each other, form a single connected or engaged entity that cannot be disconnected or disengaged (i.e. the two parts cannot be separated) without purposeful intervention by a human. Examples of suitable mechanisms include but are not limited to various fabric hook-and-loop fasteners, various metal or plastic devices having parts that clip or snap into each other, various buckles (e.g. ratchet or cam buckles), etc. However, securing means 30 could be present on only one end of the strap or be entirely eliminated in some applications (e.g. the ends of straps may be tied). Preferably, securing means 30 is of a size and shape that will be relatively flat when connected, so as to minimize discomfort to an individual wearing the device when in a prone position, i.e. with securing means 30 located underneath the individual; also a relatively small size is preferable in order to maintain the small footprint of the device. Alternatively, securing means 30 may be located on the device so that it is placed at the side or in front of an individual wearing the device. Securing means 30 must also be rugged enough to withstand the pressure that is exerted on the device, and to remain connected when the device is tightened and the bladders are inflated. While in general the device of the invention has two ends that must be secured, this need not be the case. In some embodiments, the device comprises a single closed circular band or a single closed circular entity comprising multiple interconnected straps that is placed on an individual by being pulled on over the torso, either over the head and down to a desired location, or over the feet up to a desired location. In such an embodiment, tightening means are generally present to permit adjustments to the fit of the device and the pressure exerted by the device after it is placed on an individual. In this embodiment, the material that is used in some or all of the support member may be capable of stretching to a certain extent, to allow relatively easy placement of the device. Yet the amount of "give" or "stretch" is not enough to prevent secure attachment and tightening once positioned on a patient.

In order to achieve sufficient pressure to usefully compress an area beneath an inflated bladder, the device of the invention may further comprise a tightening means 40 as depicted schematically in FIG. 1A. Tightening means 40 is highly adjustable in that adjustments to tightening means 40 or adjustments that are mediated by tightening means 40 are used to increase or decrease the tension on the flexible support portion of the device. Such adjustments should be able to be made readily and reversibly after the device is secured on an individual, and before, during and/or after bladder inflation. Increased tension throughout the support portion 10 of the device contributes to the pressure that is exerted by an inflated bladder. A device may comprise one or more tightening means 40. For example, one or more tightening means 40 may be located on each of a plurality of straps.

Figure 2:
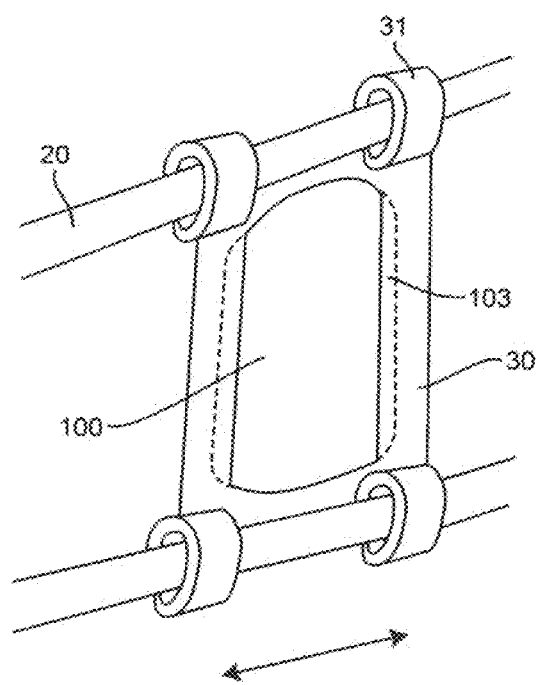
FIG. 2. Schematic representation of design allowing adjustment of location of bladder using sliding straps.

As stated above, inflatable bladders 100 are adjustable or positionable on the device. The bladders are attached to the device in a manner that is secure (i.e. they cannot be readily dislodged from the device) but that still allows adjustments to the position and/or orientation of each bladder. Adjustments to the position of a bladder can be made within certain bounds, e.g. along a certain dimension (usually, but not always, the longest dimension) of a strap or band of the device. Several mechanisms for achieving adjustability are depicted in FIGS. 2-4. However others will occur to those of skill in the art, and all such variations are encompassed by the present invention. FIG. 2 schematically represents a device of the invention in which bladder 100 is attached to straps 20 by means of sliding straps 30. Typically, two sliding straps 30 are attached to a single bladder 100 by being affixed to non-inflatable outer seam 104 of bladder 100 (see also FIG. 1E for a view of non-inflatable outer seam 104), e.g. by being sewn onto the seam, attached by an adhesive, etc. In this embodiment, each sliding strap 30 comprises two loops 31, each of which is disposed at a distal end of sliding strap 30. Loops 31 may be formed by simply folding over the ends of sliding straps 30. Alternatively, they may be attached to each end of sliding strap 30. Loops 31 encircle straps 20, thereby securing sliding straps 30, and thus attached bladder 100, to straps 20. Loops 31 encircle straps 20 loosely enough to allow movement along strap 20, as indicated by the double-headed arrow. Sliding straps 30, loops 31 and affixed bladder 100 thus move as a unit along straps 20, thereby allowing positioning or placement of bladder 100 on strap 20. When the device of the invention is worn by an individual, bladder 100 can therefore be adjusted to a position where it can most effectively exert pressure after inflation.

Figure 3A:
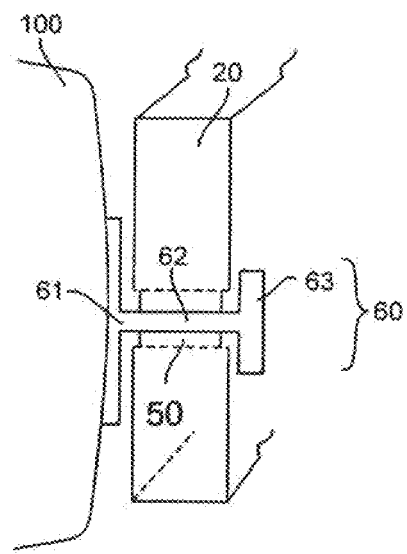
FIG. 3A-E. Schematic representation of design allowing adjustment of location of bladder. A, Cross-sectional view of belt or strap with attachment means positioned in orifice 50; B, view of the back surface of the belt or strap showing a bladder attached to the belt, and able slide along the belt between vertical barriers 70; C, multiple inflatable bladders disposed on a strap; D, a grid 400 of interconnected channels on a band of material; E, a grid 400 of interconnected channels on an arrangement of interconnected straps.
Figure 3B:
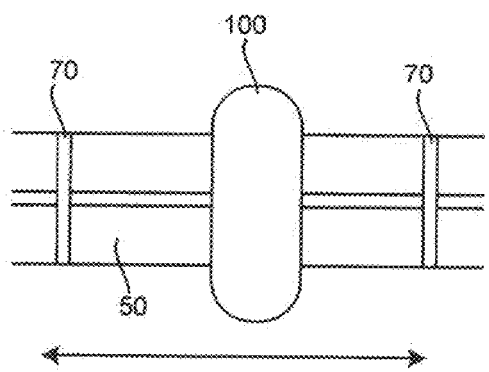
Figure 3C:
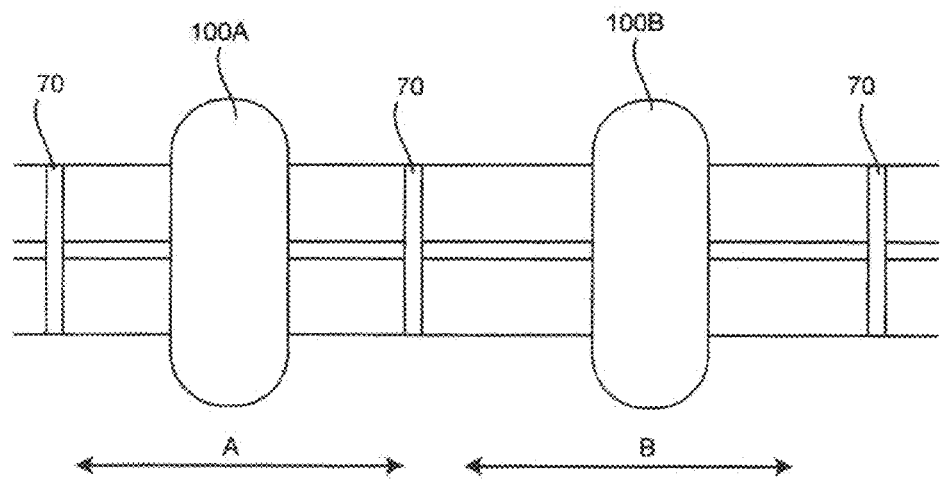
Figure 3D:
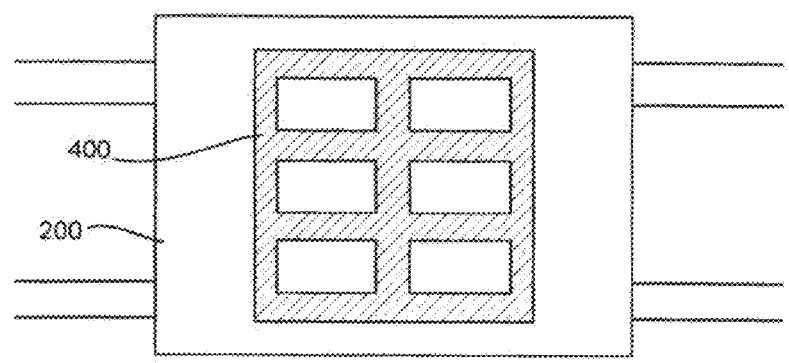
Figure 3E:
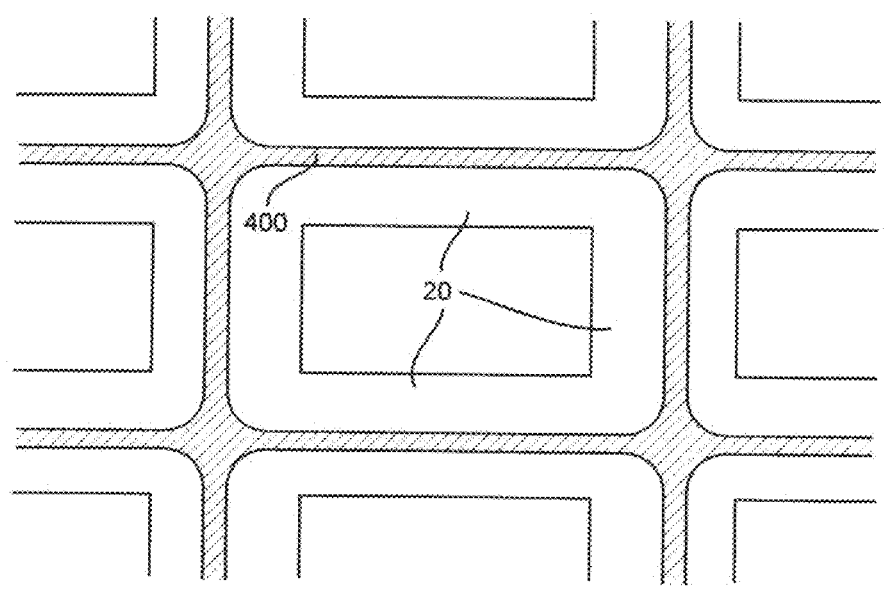

FIG. 3A illustrates a further embodiment of the invention. This figure schematically depicts a side cross sectional view of a strap 20 of the device of the invention; however, the principles discussed in this section to apply equally to band 200. Orifice 50 extends through strap 20, from an interior surface of strap 20 (the surface which faces toward which an individual wearing the device) to an exterior surface of strap 20 (the surface facing away from the individual wearing the device). Attachment means 60 comprises component 61, which attaches directly to bladder 100, stem 62, which passes through orifice 50, and attachment knob 63, which protrudes from orifice 50 onto the exterior surface of strap 20. Orifice 50 is actually an elongated opening or trough, as can be seen in FIG. 3B. Orifice 50 extends along strap 20. Engagement of attachment means 60 in this manner allows bladder 100 to be moved laterally or horizontally (with respect to the longest dimension of strap 20). Movement is restricted by barriers 70, which define the range of side to side movement of bladder 100, as shown by the double-headed arrow. Vertical barriers may be introduced by any of several known means, e.g. by sewing across the strap, by wrapping or otherwise placing material around strap 20 to form a barrier, etc. The position of bladder 100 can be adjusted along strap 20 within the bounds created by barriers 70 when device 10 is placed on an individual patient. Bladder 100 is thus mobile along strap 20. Generally, bladder 100 will be able to move a distance in the range of from about 1 to about 60 inches. Therefore, when multiple bladders are secured to strap 20, each will preferably have a defined section of strap 20 along which its position can be adjusted. This is illustrated schematically in FIG. 3C, where bladder 100A can be adjusted from side to side of the range shown by double-headed arrow A, and bladder 100B can move along the distance represented by double-headed arrow B. In this manner, when the device of the invention is placed on an individual, the positions of bladders attached to strap 20 can be adjusted as necessary or desired.

While FIGS. 2 and 3B show adjustment of a bladder horizontally with respect to the longest dimension of a strap, the movement of a bladder may also vertical, or even at a diagonal, with respect to the longest dimension of a strap to which it is moveably attached. This is accomplished by introducing a vertical or diagonal channels into a strap or band of the device, e.g. by any means described herein, or another that may occur to one of skill in the art. For example, a grid of horizontal and vertical channels may be formed to allow positioning of the bladder anywhere along the grid by slidably moving the bladder, via its attachment means, from one channel to another within the grid. This embodiment is illustrated schematically in FIG. 3D, where grid 400 formed from multiple, intersecting, connected channels is shown on a single wide band 200 of material. The number of intersecting channels may be any number, so long as they can be fit onto a support portion of the device. Further, the channels of a grid may be on several interconnected straps as illustrated schematically in FIG. 3E, where the straps themselves are shown as being arranged in a web that allows a bladder to move other horizontally or vertically from one strap 20 to another along the channels of grid 400.

Figure 4A:
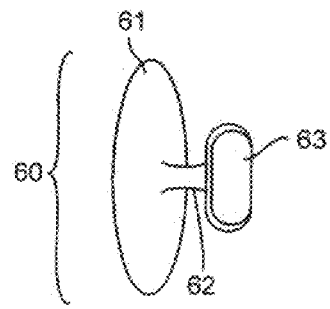
FIG. 4A-C. Exemplary attachment knobs. A, disc-like; B, rectangular; C, round.
Figure 4B:
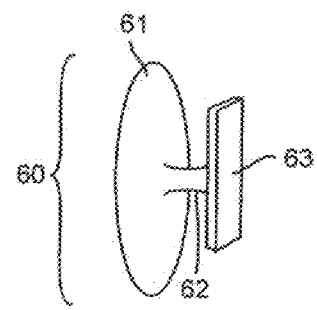
Figure 4C:
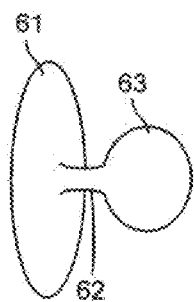

Exemplary attachment means for use in this embodiment are shown in FIGS. 4A-C. Those of skill in the art will recognize that many variants may be developed that would carry out this function, and that those depicted in FIGS. 4A-C are intended to be exemplary. Component 61 may be of any design that allows secure, direct attachment to bladder 100. Stem 62 may be of any design that allows secure, stable passage through orifice 50 and support of attachment knob 63. Attachment knob 63 may be of any shape such as disc-like (shown in FIG. 4A), rectangular (shown in FIG. 4B), round (shown in FIG. 4C), etc., so long as this portion of attachment means 60 is large enough to be retained within orifice 50. In addition, attachment knob 63 may be capable of being tightened so as to secure the bladder at the desired position. Various tightening or locking mechanisms are known to those of skill in the art, e.g. attachment means 63 may be threaded onto stem 62 and may be screwed down to tighten it.

Figure 5A:
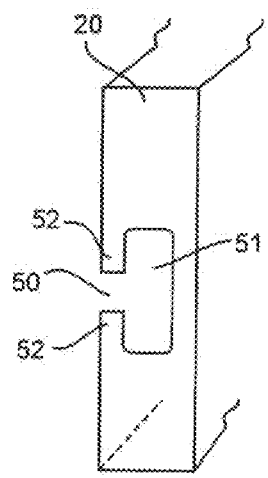
FIGS. 5A and B. Exemplary embodiment of the invention. A, cross sectional view of strap with internal elongated chamber; B, bladder attached to the strap.
Figure 5B:
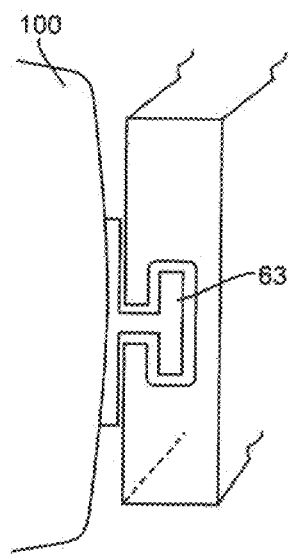

Those of skill in the art will recognize that other variants of the device also can be developed. For example, In FIG. 5A, strap 20 is shown with orifice 50 leading to opening or chamber 51. Chamber 51 is located within the interior of strap 20 and runs horizontally along the length of strap 20, i.e. it is elongated within strap 20. When viewed from the back of strap 20, the orifice runs along strap 20 and appears as an open slit leading into elongated chamber 51, which forms a trough within strap 20. Chamber 51 is large enough to allow attachment knob 63 to slide laterally (horizontally with respect to the longest dimension of strap 20) within elongated chamber 51, allowing lateral (horizontal) movement of bladder 100 along strap 20. However, as discussed above, channels such as elongated chamber 51 may be placed in a vertical (or even diagonal) position, e.g. in a grid formation, to allow movement of the bladders within the X-Y plane of the device. Strap 20 may be manufactured with bladders attached in this manner. Alternatively, flaps 52 that define orifice 50 may be somewhat flexible and sufficiently deformable to allow placement and removal of attachment means 60, yet rigid enough to hold attachment knob 63 within chamber 51 in the absence of a purposeful attempt by a user of the device to dislodge attachment knob 63 from chamber 51. In addition, in this embodiment vertical barriers 70 may be introduced by any of several known means, e.g. by sewing across the strap, by filling chamber 51 with a solid substance, by wrapping or otherwise placing material around strap 20 to form a barrier, etc. Thus, in this embodiment, bladder 100 can be moved through a defined distance on strap 20, the distance being bounded by barriers 70.

Figure 6A:
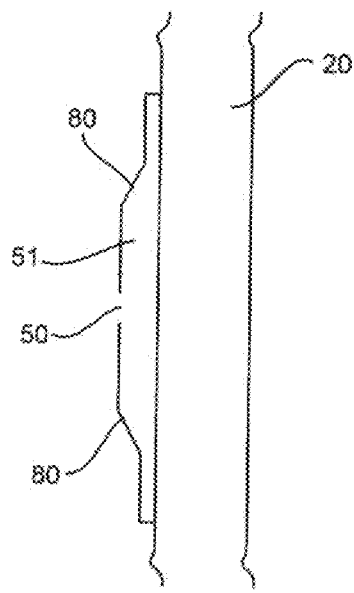
FIG. 6A-B. Exemplary embodiment of the invention. A, cross sectional view of strap with channel forming member attached to interior of strap; B, bladder attached to strap.
Figure 6B:
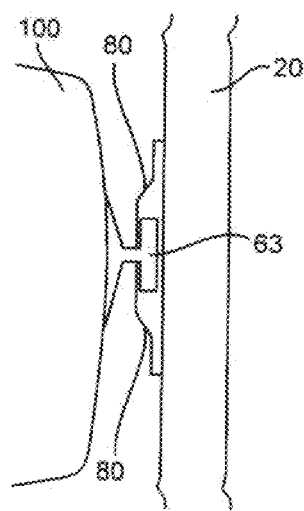

Those of skill in the art will be aware of other possible designs for moveably attaching inflatable bladders to the device described herein. For example, a molded elongated trough or channel for receiving attachment knob 63 may be attached to the interior surface of strap 20, as shown in the cross sectional view provided in FIGS. 6A and B. In this case, chamber 51 is created by flaps 80. When attachment knob 63 is ensconced within chamber 51, bladder 100 is free to glide through the trough and along the surface of strap 20. Movement may be either horizontal, vertical, or diagonal, depending on the position of the channels. Flaps 80 may be constructed of any suitable material, and may be fashioned, for example, from metals, plastics, rigid strapping material, etc. As is the case for other embodiments, barriers 70 may be placed along the trough or channel to provide end points for the range of movement of the attached bladder.

The design of the device is not limited to bladders whose positions can be adjusted horizontally. Rather, vertical and/or diagonal elongated chambers may be introduced to allow vertical and/or diagonal adjustments of bladders in a manner similar to that described for horizontal adjustments. In addition, the depictions herein show bladder 100 attached to a single strap 20. This design has an advantage in that, in addition to allowing bladder 20 to be moved from side to side along strap 20, bladder 20 can also be rotated around stem 62 and thus placed at an angle, if warranted. In other embodiments of the invention, bladder 100 may be attached to multiple straps 20. Each strap 20 to which bladder 100 is attached is provided with a means to allow attachment and movement as described herein but along two or more straps simultaneously. Also, in this embodiment, bladder 100 is fitted with a plurality of attachment means 60, typically one for each strap to which it is to be attached, or sliding straps 30 and loops 31, typically 2 and 4 of each, respectively, for each two straps to which a bladder is attached.

While in some embodiments each bladder 100 is individually adjustable, in other embodiments two or more bladders 100 may be joined to each other in tandem, and moved as a unit.

The device of the invention may be used in any situation where it is desirable to provide an individual (e.g. a patient) with a source of intense, directed pressure. For example, to quell bleeding, particularly from a difficult to compress area such as the pelvis or groin, the device may be applied to an injured individual and bladders positioned and inflated directly over the most suitable area(s). This is illustrated schematically in FIG. 7A, which shows an individual wearing the device of the invention, and inflated bladder 100 positioned so as to occlude the femoral artery upon inflation. The straps may be tightened to simultaneously stabilize the boney pelvis.

However, the device of the invention is also useful as an adjunct to CPR. After a cardiac arrest, it is extremely important to reestablish blood circulation to the heart and brain as soon as possible, whereas blood flow to the extremities is not immediately crucial. Conventional CPR is performed by intermittently compressing on the chest in order to produce adequate coronary and cerebral perfusion. Blood flow to the abdominal organs is not required to resuscitate the patient with cardiac arrest. Use of the present invention by placement and inflation on the abdomen may prevent blood movement from the chest cavity into the abdominal cavity thus redirecting blood and blood pressure back towards the heart and brain. In one derivation of this strategy the device is engaged and a bladder which approximately overlies the abdominal aorta is inflated. This configuration allows selective increase in aortic pressure over vena caval pressure thus enhancing coronary perfusion pressure during chest compressions. Alternatively, the device may be placed around the chest and activated. In this manner the chest is not allowed to expand during positive pressure ventilation. Thus during positive pressure ventilation, the pressure within the thoracic cavity is enhanced thus causing increased blood flow movement to the head and potentially heart. If an additional device is placed over the abdomen and engaged, the added advantage of reducing abdominal blood flow during CPR accrues, as well as allowing for maximal redirection of blood flow to the heart and brain.

Therefore, it may be beneficial to apply pressure to the chest and abdominal cavity and to enhance critical myocardial and cerebral perfusion until proper cardiac function is reestablished. The device of the invention is highly suitable for doing so, especially in emergency situations. The device may be deployed around the chest of a patient as illustrated in FIG. 7B and/or around the abdomen. Further, in some embodiments of the invention, the device may be large enough to span the chest, abdomen, and pelvis. In this case, bladder inflation may occur in one or more or all three regions of the device, as dictated by the type of condition or injury sustained by the patient. This embodiment is illustrated in FIG. 7C, which shows multiple belts 20 with attached inflatable bladders 100 across the chest, abdominal, and pelvic regions of a patient.

The invention also provides a method of controlling hemorrhage from blood vessel(s) (usually an artery) located in areas that are difficult to compress in an individual in need thereof. The method involves placing the device of the invention on the individual and positioning a bladder of the device at a location directly over an area which, when compressed, will constrict the artery that is damaged and bleeding. Thereafter, the bladder is inflated to a pressure sufficient to compress the area and control (e.g. stop or decrease) the hemorrhage.

The invention also provides an adjunct to CPR for an individual in need thereof. In this embodiment of the invention, the device of the invention is placed on the individual so as to encircle at least the chest and/or abdomen. This embodiment of the invention does not necessarily require the precise positioning of the bladders. Rather, all bladders present in the device are inflated to a pressure in the range of from about 100 to about 500 mmHg.

The invention is further illustrated in the non-limiting examples provided below.

EXAMPLES

Example 1

Reduction and Elimination of Blood Flow in Femoral Artery

Figure 7A:
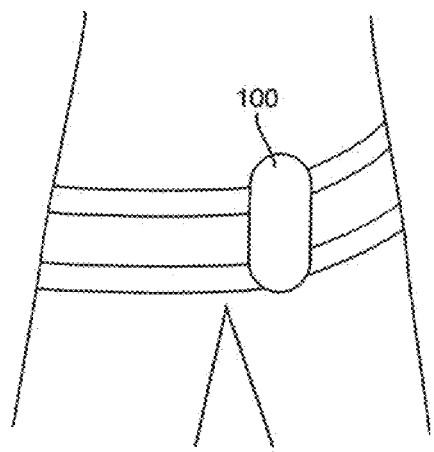
FIG. 7A-C. Device attached to an individual. A, attachment in the pelvic region; B, attachment to the chest; C, device attached to chest, abdominal and pelvic regions.
Figure 7B:
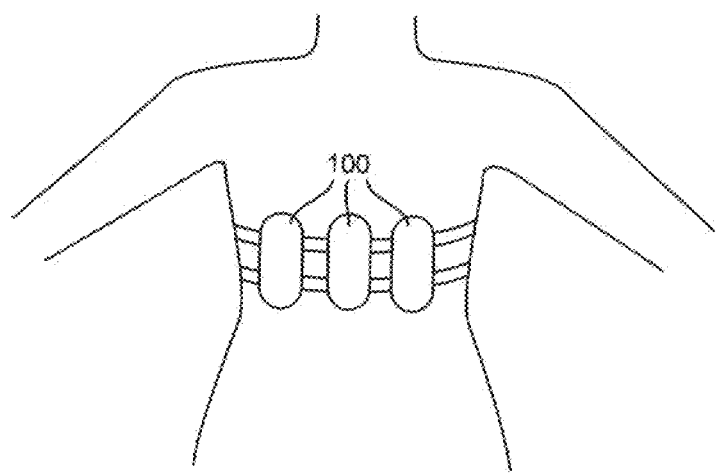
Figure 7C:
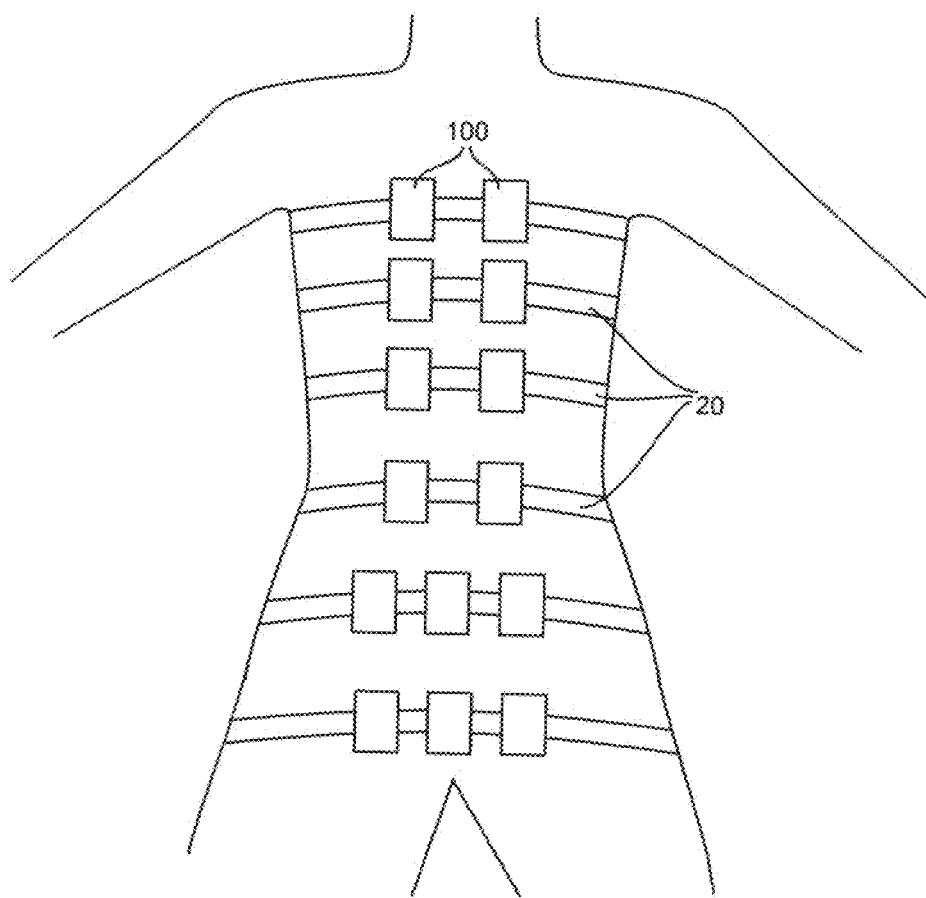

The compression device of the invention was attached to a human subject so that the inflatable bladders rested against the groin, as illustrated schematically in FIG. 7A. One inflatable bladder was inflated to approximately 300 mmHg using hand bulb pump mechanisms; inflation pressure was monitored using an aneroid manometer. The flow of blood through the femoral arteries was monitored using Doppler ultrasound.

The results of applying pressure on the region of the left femoral artery by bladder inflation showed no blood flow and the elimination of pulsatile flow after inflation of the bladder. These effects were reproducible in both femoral arteries with approximately 200-300 mm Hg inflation pressure. When both bladders were inflated, more than 200-300 mm Hg was required to eliminate blood flow. The "medic finger" model can explain this observation: when the additional bag was inflated, tension on the first bag was decreased. Therefore, more pressure was required.

Example 2

In Vivo Demonstration of Hemorrhage Control

A 40 kg swine was previously instrumented with an abdominal aortic flow probe which measures blood flow going through the abdominal as it exits below the diaphragm. The animal is also instrumented with an arterial catheter in the carotid artery to measure arterial blood pressure and a central venous catheter is placed into the superior vena cava via the external jugular vein to measure central venous pressure (CVP).

The compression device of the invention was placed around the closed abdomen and snuggly secured. Baseline readings were taken at 13:45. The device was rapidly inflated causing the inflatable members to expand downward towards and in toward the abdominal wall, thereby directing pressure into the abdominal cavity. Hemodynamic measurements were taken from 13:45:30 to 13:47:30 and the results are presented in Table 1. The results demonstrate significant reductions abdominal aortic blood flow with a simultaneous increase in carotid artery pressure, while CVP was not significantly changed. At 13:47:57, the device was disengaged by deflating the inflatable members. As noted, aortic blood flow increases immediately after deflation.

TABLE 1

| | | Time 13:45:00 Deflated | | | Time 13:47:30 Inflated | |
|---|---|---|---|---|---|---|
| Arterial | Systolic peak | 94 | mmHg | Arterial Systolic peak | 124 | mmHg |
| | Diastolic peak | 81 | mmHg | Diastolic peak | 75 | mmHg |
| CVP | Systolic peak | 8.3 | mmHg | CVP Systolic peak | 9.6 | mmHg |
| | Diastolic peak | 7.9 | mmHg | Diastolic peak | 8.1 | mmHg |
| Aortic | Systolic peak | 2.12 | ml/min | Aortic Systolic peak | 0.71 | ml/min |
| Flow | Diastolic peak | 1.50 | ml/min | Flow Diastolic peak | 0.42 | ml/min |
| | | Time 13:45:30 Inflated | | | Time 13:47:57 Deflated | |
| Arterial | Systolic peak | 120 | mmHg | Arterial Systolic peak | 85 | mmHg |
| | Diastolic peak | 73 | mmHg | Diastolic peak | 59 | mmHg |
| CVP | Systolic peak | 9.3 | mmHg | CVP Systolic peak | 8.3 | mmHg |
| | Diastolic peak | 7.8 | mmHg | Diastolic peak | 8.2 | mmHg |
| Aortic Flow | Systolic peak | 1.32 | ml/min | Aortic Flow Systolic peak | 1.54 | ml/min |
| | Diastolic peak | 0.69 | ml/min | Diastolic peak | 1.0 | ml/min |

Since during this experiment, aortic blood flow was measured at a point before any major branches come from it to supply blood to the abdominal organs, the reduction in aortic blood flow that was observed when the device was activated would result in decreased blood flow to these organs and thus less hemorrhage from trauma.

Example 3

In Vivo Demonstration of Usefulness of the Apparatus as an Adjunct to CPR

In this example, a 40 kg swine was instrumented as described in Example 2 above. However, the device of the invention was place around the animal's chest. A state of cardiopulmonary arrest was produced by injection of potassium chloride while the animal was anesthetized with alpha choralose. Various parameters were measured as in Example 2, and are presented in Table 2.

TABLE 2

| Time 13:53:18 Deflated | | Time 13:56:00 Inflated | |
|---|---|---|---|
| Arterial | 32 mmHg | Arterial | 45 mmHg |
|  | 23 mmHg |  | 40 mmHg |
| CVP | 8.4 mmHg | CVP | 9.5 mmHg |
|  | 7.2 mmHg |  | 8.4 mmHg |
| Aortic Flow | 0 | Aortic Flow | 0.14 ml/min |
|  | 0 |  | 0.17 ml/min |
| CPP | 15.8 mmHg | CPP | 31.6 mmHg |

| Time 13:54:00 Inflated | | Time 13:56:30 Deflated | |
|---|---|---|---|
| Arterial | 49 mmHg | Arterial | 17.6 mmHg |
|  | 41 mmHg |  | 12.8 mmHg |
| CVP | 9.7 mmHg | CVP | 6.6 mmHg |
|  | 8.5 mmHg |  | 6.3 mmHg |
| Aortic Flow | 0.37 ml/min | Aortic Flow | 0.01 ml/min |
|  | 0.07 ml/min |  | 0.01 ml/min |
| CPP | 32.5 mmHg | CPP | 6.5 mmHg |

Time 13:53:18 shows hemodynamic parameters after cardiac arrest with only ventilation with a mechanical ventilator at a tidal volume of 10 cc/kg and a rate of 12 breaths per minute. Of note is that coronary perfusion pressure (CPP) is the difference between arterial diastolic pressure and central venous diastolic pressure. CPP is the main hemodynamic determinant of successful resuscitation with higher values promoting successful resuscitation. This occurs since higher CPP produces more blood flow through the coronary circulation of the heart. At 13:54:00 the compression device was activated by inflating the inflatable members. This forces the members against the sides of the chest and sternum. In effect, this prevents the chest from expanding during ventilation. As ventilation continues, the inflation of the lungs caused the intrathoracic pressure to significantly increase. As can be seen, as a result, both aortic blood flow and CPP improved significantly. At 13:56:30 the device was deactivated. After this occurs, the aortic blood flow and CPP drastically decreased.

These pressure changes were created without the need for chest compression. Use of such a device on both the chest and the abdomen during cardiac arrest may be useful in maximizing CPP. Furthermore, use of the device on the abdomen alone in conjunction with chest compressions may be beneficial in enhancing hemodynamics and therefore conducive to successful resuscitation.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A medical compress device comprising:
    a support member circumferentially securable to any area of a body of a patient, said support member having at least two ends separated by a length dimension;
    one or more inflatable bladders attached to said support member, said inflatable bladders being selectively inflatable and deflatable, each of said one or more inflatable bladders being positionable at multiple locations from one of said at least two ends to the other of said at least two ends along said length of said support member, whereby when said at least two ends of said support member are joined together to attach said support member to said patient and said one or more inflatable bladders are positioned at one or more selected locations of said multiple locations along said length of said support member and are inflated, a compressive force is exerted on at least one specific area on said patient and said one or more inflatable bladders remain adjustable along the length dimension during exertion of the compression force and after said support member is attached to said patient; and
    at least one tightening member associated with at least a portion of said support member for tightening said support member on said patient after said at least two ends of said support member are joined together,
    wherein said support member is comprised of one or more belts,
    wherein said support member includes a channel formed in said one or more belts which extends from one of said at least two ends to the other of said at two ends along said length of said support member, and wherein said one or more inflatable bladders includes an attachment knob which includes a portion which fits within said channel.

2. The medical compress device of claim 1 wherein said one or more bladders have length and width dimensions which are different from each other, and wherein said one or more bladders are rotatable about said attachment knob relative to said one or more belts.

3. The medical compress device of claim 1, wherein said channel forms a grid.

4. A medical compress device, comprising:
    a support member circumferentially securable to any area of a body of a patient, said support member having at least two ends separated by a length dimension;
    one or more inflatable bladders attached to said support member, said inflatable bladders being selectively inflatable and deflatable, each of said one or more inflatable bladders being positionable at multiple locations from one of said at least two ends to the other of said at least two ends along said length of said support member, whereby when said at least two ends of said support member are joined together to attach said support member to said patient and said one or more inflatable bladders are positioned at one or more selected locations of said multiple locations along said length of said support member and are inflated, a compressive force that directs pressure into into a groin or pelvic cavity is exerted on at least one specific area on said patient and said one or more inflatable bladders remain adjustable along the length dimension during exertion of the compression force and after said support member is attached to said patient; and
    at least one tightening member associated with at least a portion of said support member for tightening said support member on said patient after said at least two ends of said support member are joined together; and
    wherein the compressive force compresses blood vessels in the at least one specific area on said patient to reduce uncontrolled bleeding,
    wherein said support member is comprised of one or more belts, and
    wherein said support member includes a channel forming member attached to said one or more belts which extends from one of said at least two ends to the other of said at two ends along said length of said support member, and wherein said one or more inflatable bladders includes an attachment knob which includes a portion which fits within said channel forming member.

5. The medical compress device of claim 4 wherein said one or more bladders have length and width dimensions which are different from each other, and wherein said one or more bladders are rotatable about said attachment knob relative to said one or more belts.

6. The medical compress device of claim 4, wherein said channel forming member forms a grid.

7. A method for exerting a compressive force at least one specific area on a patient in need thereof, comprising the steps of
   i) circumferentially attaching to any area of a body of said patient a medical compress device, comprising:
   a support member, said support member having at least two ends separated by a length dimension;
   one or more inflatable bladders attached to said support member, said inflatable bladders being selectively inflatable and deflatable, each of said one or more inflatable bladders being positionable at multiple locations from one of said at least two ends to the other of said at least two ends along said length of said support member; and
   at least one tightening member associated with at least a portion of said support member;
   wherein said step of attaching includes a step of joining together said at least two ends of said support member;
   ii) positioning said one or more inflatable bladders at one or more selected locations of said multiple locations along said length of said support member, wherein said one or more selected locations at least partially covers said at least one specific area on said patient;
   iii) inflating said one or more inflatable bladders at one or more selected locations, whereby said step of inflating causes a compressive force to be exerted at said at least one specific area on said patient, said compressive force maintaining a pressure of at least 180 mmHg, and wherein the at least one tightening member is adjustable during application of the compressive force; and
   iv) adjusting said at least one tightening member for tightening said support member on said patient after said two ends of said support member are joined together,
   wherein said method is used to control hemorrhage.

8. The method of claim 7, wherein said method is used as an adjunct to cardiopulmonary resuscitation (CPR).

9. The method of claim 7, wherein at least one of said one or more inflatable bladders is automatically inflated or deflated based on vital signs for said patient, said vital sign being one of heart rate and pulse.

10. The method of claim 7, wherein the method is used to simultaneously provide compression to control bleeding within a pelvic cavity and to stabilize a fractured pelvis.

11. A medical compress device, comprising:
   a support member circumferentially securable to any area of a body of a patient, said support member having at least two ends separated by a length dimension;
   one or more inflatable bladders attached to said support member, said one or more inflatable bladders being selectively inflatable and deflatable, each of said one or more inflatable
   bladders being positionable at multiple locations along a channel which extends from one of said at least two ends to the other of said at two ends along said length of said support member, wherein said one or more inflatable bladders includes an attachment knob which includes a portion which fits within said channel,
   whereby when said at least two ends of said support member are joined together to attach said support member to said patient and said one or more inflatable bladders are positioned at one or more selected locations of said multiple locations along said length of said support member and are inflated, a compressive force is exerted on said patient at least one specific area on said patient and said one or more inflatable bladders remain adjustable along the length dimension during exertion of the compression force and after said support member is attached to said patient.

* * * * *